United States Patent [19]
Babirad et al.

[11] Patent Number: 5,639,843
[45] Date of Patent: Jun. 17, 1997

[54] ORGANOMETALLIC ACRYLAMIDE COMPOSITIONS AND METHODS FOR MAKING SAME, INCLUDING ANTIFOULING AGENTS AND USAGE THEREOF

[75] Inventors: Stefan A. Babirad, Hudson, Wis.; W. Stuart Bigham, Mahtomedi, Minn.

[73] Assignee: Minnesota Mining and Manufacturing Company, St. Paul, Minn.

[21] Appl. No.: 180,882

[22] Filed: Jan. 12, 1994

[51] Int. Cl.$^6$ .................. C07F 7/22; C07F 7/24; C07F 7/30; C07C 239/00
[52] U.S. Cl. .................. 528/9; 528/370; 528/406; 528/407; 528/485; 528/488; 528/490; 64/134; 64/152; 64/153; 556/87; 556/31; 544/90
[58] Field of Search .................. 528/9, 370, 406, 528/407, 485, 488, 490; 564/134, 152, 153; 556/31; 544/90

[56] References Cited

U.S. PATENT DOCUMENTS

| | | | |
|---|---|---|---|
| 4,021,392 | 5/1977 | Milne et al. | 427/409 X |
| 4,820,748 | 4/1989 | Yamamori et al. | 523/122 |
| 4,852,969 | 8/1989 | Babirad et al. | 350/96.34 |
| 4,952,612 | 8/1990 | Brown-Wensley et al. | 522/25 |
| 4,996,243 | 2/1991 | Rasmussen et al. | 522/99 |
| 5,147,957 | 9/1992 | Kumar | 528/15 |
| 5,192,451 | 3/1993 | Gill | 210/755 |
| 5,192,603 | 3/1993 | Slater et al. | 428/217 |
| 5,200,471 | 4/1993 | Coleman et al. | 525/326.9 |
| 5,246,913 | 9/1993 | Hsu | 504/156 |
| 5,292,840 | 3/1994 | Heilmann et al. | 526/304 |
| 5,321,095 | 6/1994 | Greenwald | 525/404 |

OTHER PUBLICATIONS

Brown and Lemay, "Chemistry, the Central Science," 2nd ed., 1981, Periodic table of the Elements.

"The Vocabulary of Organic Chemistry", M. Orchin, John Wiley & Sons: New York, 1980, p. 432, def'n. 12.100.

"Surface Coatings", Prep'd by Oil and Colour Chemists' Assoc., Australia, vol. 2–Paints and Their Applications, 2nd ed. London, 1984, pp. 508–514.

"Surface Coatings–1", edited Alan Wilson, J.W. Nicholson & H.J. Prosser, Elsevier Applied Science Publ. Ltd.: London, 1987, pp. 17–67.

Encyclopedia of Polymer Science and Engineering, vol. 11, 2nd. ed., "Polyazlactones", John Wiley & Sons: New York, 1988, pp. 558–571.

J.J. Cooney and S. Wuertz, Journal of Ind. Microbiology, 4 (1989), pp. 375–402, "Toxic effects of tin compounds on microorganisms".

R.R. Joshi and S.K. Gupta; Proceedings of the ACS Div. of Polymeric Materials: Science and Engineering, vol. 62, Spring 1990, pp. 654–657.

A.S. Clare et al., Invertebrate Reproduction and Development, 22:1–3 (1992), pp. 67–76, "Molecular approaches to nontoxic antifouling".

Huber et al, Applied Organometallic Chemistry, vol. 7, 243–252, (1993).

Shcherbakou et al., Synth. React. Inorg. Met. Og. Chem. 21(10) 1549–1567 (1991).

Sandhu et al., Main Group Met. Chem. 31(1) 29–50, (1990).

Joshi et al, Toxicol. Envirou. Chem. 34(2–4) 133–138, (1992).

Klein et al., Monatsch. Chem (1992) 123(8–9) 801–806.

*Primary Examiner*—Matthew V. Grumbling
*Attorney, Agent, or Firm*—Gary L. Griswold; Walter N. Kirn; Gregory D. Allen

[57] ABSTRACT

The present invention relates to novel reaction products of azlactones and organometallic nucleophiles and the method of making these reaction products. The invention also relates to methods of using such reaction products to prevent or eliminate microbial and fungal growth on substrates. Reaction products can be provided that show improved antifouling and antimicrobial action.

6 Claims, No Drawings

ORGANOMETALLIC ACRYLAMIDE COMPOSITIONS AND METHODS FOR MAKING SAME, INCLUDING ANTIFOULING AGENTS AND USAGE THEREOF

BACKGROUND OF THE INVENTION

1. Field of the Invention

This invention relates to novel organometallic acrylamide compositions that result from the reaction of an azlactone and an organometallic nucleophile. The reaction products of the invention encompass compositions that are especially useful as antifouling and antimicrobial agents.

2. Description of the Related Art

The fouling of surfaces in marine and terrestrial environments has been a long standing problem. Submerged marine substrates in aqueous media such as ship-bottoms, oil platforms, fishing nets, and floodgates have been scarred by microbes including arthropods such as barnacles, coelenterates such as hydras, annelids such as hydroides, diatoms such as fine algae, blue-green algae, green algae, brown algae, and various kinds of bacteria colloquially referred to as slime. These fouling problems, traditionally most acute in the oceans and seas, have extended even into fresh water bodies such as the Great Lakes of North America which have experienced an infestation by mollusks, commonly referred to as zebra mussels (*Dreissena polymorpha*163 ). These mollusks pose a serious problem to submerged aquatic substrates upon which they attach.

On the other hand, terrestrial substrates, such as statues, stone monuments, signs, building facades, tombstone markers, wood decking and rooftops are also prone to fouling by algae growth in particular. Large expenditures of resources are devoted by private, public and commercial interests in attempts to combat these microbial and fouling problems.

For example, the removal of microbes can be implemented by mechanical cleaning. However, this mode of restoration of surfaces after they have already been attacked by microbes can be costly, and it also can create health and safety hazards to the workers. As can be understood, preventive measures would be more desirable in many cases in combating microbial growth as opposed to taking remedial action. Towards this end, the application of antifoulant paints or coatings as a pretreatment of surfaces susceptible to fouling or microbial growth problems has come into widespread usage as a method to discourage and control microbe infestation. More detailed information concerning antifoulant paints and coatings is described by A. D. Wilson, J. W. Nicholoson, and H. J. Prosser, "Surface Coatings-1", Elsevier Applied Science Publishers LTD : New York, 1987, pp. 17–67; and "Surface Coatings Vol. 2-Paints and Their Applications", Chapman and Hall LTD: New York, 1984, pp. 508–514.

Numerous developments of novel antifouling systems have been proposed. For instance, in U.S. Pat. No. 5,192,451, the use of a water soluble dialkyl diallyl quaternary ammonium polymer (polyquat) is reported to be effective in controlling zebra mussels in ship ballasts. U.S. Pat. No. 5,192,603 teaches an elastomeric undercoat used to reinforce a fouling resistant silicone rubber topcoat. Clare et al. reported investigations on naturally-occurring molecular approaches to providing nontoxic antifoulants in *Invertebrate Reproduction and Development*, 22:1–3, 67, 1992. Clare et al. discuss the use of certain diterpenes extracted from living organisms as barnacle settlement inhibitors, but, concluded that the potential costs in either isolating in sufficient quantity or synthesizing these compounds was prohibitive to their commercial use as antifoulants.

In general, certain organometallic compounds including copper, zinc, and tin as central atoms have also been incorporated within antifouling systems as biocides. Many of the known organotin biocide compounds are described by A. D. Wilson, J. W. Nicholoson, H. J. Prosser, "SURFACE COATINGS - 1", Chapter 2: "Organotin-Based Antifouling Sysytems," Elsevier Applied Science Publishers LTD: New York, 1987, pp. 17–67; and "Surface Coatings Vol. 2 - Paints and Their Applications", Chapman and Hall LTD: New York, 1984, pp. 508–514. These biotoxins are thought to prevent fouling by interfering with the ability of marine organisms to attach to submerged structures, either by weakening or killing the organism.

Typical antifouling paints contain one or more marine biotoxins which are dispersed in a resin carrier, such as disclosed in U.S. Pat. No. 5,246,913. To achieve a lethal concentration of biotoxin to microbes at the water-substrate interface, such paints rely on diffusion of the biotoxin through the resin to the paint surface. There is a drawback observed, however, in that the rate of diffusion of the biotoxin from the surface into the surrounding water is much faster than the replenishing rate of diffusion of the biotoxin from the bulk resin to the surface. As a consequence of this diffusion rate dynamic, the surface concentration of biotoxin drops below the lethal limit needed to effectively prevent microbial growth thereon before all of the biotoxin in the paint is depleted.

Trisubstituted alkyl and aryl tin compounds are generally more toxic than di- or mono- substituted organotins. Among trisubstituted organotin compounds, propyl, butyl, pentyl, phenyl, and cyclohexyl moieties are generally considered the most toxic to microorganisms. The action of these molecular species as it relates to biocidal activity is described by J. J. Cooney and S. Wuertz in *J. Ind. Microbiol.*, 4, 375, 1989. In particular, nonpolymerized tributyl tin compounds have been used extensively in the last decade as antifouling agents due to their high activity against algae and fungus. Inadvertent run-off and excessive marine applications of tributyl tin compounds are now linked to adverse environmental effects which have not gone unnoticed by regulatory authorities in a number of countries. In fact, in 1988, the United States' Environmental Protection Agency (EPA) classified tributyl tin compounds as restricted-use pesticides, and it presently is illegal to use tributyl tin compounds in antifouling systems such as marine paints.

Recent advances have been made to develop ablative or "self-polishing" paints that typically utilize biocidal polymers based on (meth)acrylic acid which has been esterified with bis(tributyltin) oxide. This method reportedly reduces the toxicity of tributyl compounds by attaching the biocide to a polymeric backbone. In the thus-formed polymers, such as described in U.S. Pat. No. 4,012,392, a slow hydrolysis of the tin ester in water is provided to not only release the biotoxin into the surrounding aqueous environment but which also causes the gradual disintegration and sloughing off of the outer layer of the paint; thereby continuously replenishing the amount of available biotoxin at the water-surface interface. One drawback of these above compounds are that the moieties on the organotin species are not considered maximal for achieving the most efficient antifouling action. Furthermore, (meth)acrylates often polymerize at slow rates and provide polymers with the biocide which possess inadequate thermal and hydrolytic stabilities.

The synthesis of a tributyltin-4-acryloylamino benzoate and the effect of an incorporated 4-amino benzoic acid as a spacer group on fouling has been reported by R. R. Joshi and S. K. Gupta, *Polym. Mater. Sci. Eng.*, 62, 654, (1990). The monomer and homopolymer formed by the methods of Joshi et al. are reported to show maximum toxicity towards *Sarcina lutea* and *Pseudomonas aeruginosa*, respectively. The monomer is described by Joshi et al. as prepared by a multi-step scheme involving esterfication of p-aminobenzoic acid with tributyltin oxide in a dry benzene solvent followed by amidation in the presence of acryloyl chloride in a dry benzene solvent. The polymer thereof is described by Joshi et al. as prepared by polymerizing the monomer with 2-2'-azobisisobutyro-nitrile in 1,4 dioxane. However, the multi-step reaction needed by Joshi et al. to form the monomer is burdensome and onerous. The methodology of Joshi et al. is complicated by the necessary removal and precautions which must be taken to handle the hydrogen chloride by-product generated, and by the use of benzene as solvent. Naturally, a facile one-step synthesis scheme to form either the monomer or polymer which avoids troublesome by-products and solvents would be more desirable.

In general, 2-alkenyl azlactones have been reported to react with certain nucleophiles, such as primary amines and alcohols to afford (meth)acrylamide-functional products. A thorough discussion of the ring-opening reactions of azlactones with certain nucleophiles can be found in a review article by J. K. Rasmussen, S. M. Heilmann, and L. R. Krepski, entitled "POLYAZLACTONES", *Encycl. Poly. Sci. Eng.*, 11, 558–571, 1988. However, this report does not indicate that organometallic nucleophiles, such as organotin nucleophiles, are adaptable or suited to the chemistry.

U.S. Pat. No. 4,852,969 to Babirad et al. discloses silanols as reacted with 2-alkenyl azlactones in a nucleophilic addition reaction to yield silyl 2-amidoacetates and silyl 3-propionates. However, these silicon-based nucleophiles are not recognized as biocides and they do not provide antifouling or antimicrobial action. Instead, the reaction products of the above-mentioned Babirad et al. patent were stated to be useful as a means of providing well-adhering claddings to siliceous cores for light transmission in a fiber optics construction. Further, the Babirad et al. disclosure does not suggest the use of nucleophiles other than certain silanols. These silanols are customarily characterized as metalloids, and do not come under the traditional definition of organometallic materials, such as defined by Orchin et al., "THE VOCABULARY OF ORGANIC CHEMISTRY," John Wiley & Sons, New York, 12.100, page 432, 1980.

More recently, U.S. Pat. No. 5,246,913 to Hsu describes a use of non-organometallic-based synergistic antimicrobial and biocidal composition comprising 5-chloro-2-methyl-4-isothiazolin-3-one and 2-methyl-4-isothiazolin-3-one and one or more commercial biocides to purportedly provide a more effective and broader control of microorganisms in various industrial systems.

U.S. Pat. No. 4,820,748 to Nippon Paint Co., Ltd. indicates that germanium esters of methacrylic acid are effective against marine algae.

It is believed that the reaction of an azlactone and a organometallic nucleophile to provide a reaction product, including a product affording antifouling or antimicrobial action, has not been previously reported.

SUMMARY OF THE INVENTION

Briefly, the present invention involves a new chemical reaction to form organometallic acrylamide products. Among other things, the new method can be used to form reaction products that are efficient antifouling and antimicrobial agents.

In one embodiment, the reaction products of the invention are prepared by a new reaction of azlactones and organometallic- alcohols, thiols or amine reactants. These reaction products are formed by a nucleophilic addition of a soluble, low or high molecular weight reactant containing one or more organometallic alcohol, thiol or amine groups to a soluble or insoluble, low or high molecular weight reactant containing one or more azlactone groups. The reaction of the invention is highly efficient due to its one step scheme to completion. Therefore, the method of the invention can be performed in a facile one pot procedure. Further, the reaction of the invention is advantageous as it can be conducted solvent-free ("neat") and without the formation of bothersome by-products.

Other advantages of the invention are that the organometallic acrylamides formed by the method of the invention have an acrylamide polymerizable head group or monomer, such as vinyl azlactone or a 2-alkenyl azlactone copolymer, described in greater detail hereinafter, which provides the advantage of faster polymerization rates when compared to (meth)acrylates. The acrylamide functionality is a more hydrolytically stable linkage than the ester linkage in (meth)acrylates, giving rise to a more environmentally stable polymer. The acrylamide functionality also gives enhanced adhesion to inorganic substrates due to potential hydrogen-bonding capabilities of the amino moiety which is lacking in the ester derivatives of (meth)acrylate systems.

In a further embodiment of the invention, there are provided reaction products of a organometallic nucleophile and an azlactone which are effective antifouling and antimicrobial ingredients. These ingredients can be utilized in marine paints and coatings or as topical coatings on terrestial construction materials. Preferably in this embodiment, the central metal atom of the triorganometallic nucleophile is a tin (Sn) atom. These antifoulant compounds of the present invention have favorable toxicity against the targeted fouling organisms such as algae and fungus. Further, these compounds can efficaciously retard growth and, in some cases, even attachment, of fouling organisms and microbes on the surfaces of substrates but with a lessened tendency of the agent to migrate away from the treated surface into the surrounding environment.

In one preferred embodiment, the three substituents of the organometallic compound, other than the nucleophilic group, are selected to all represent an organo substituent of alkyl or aryl. This preference arises out of the fact that the trialkyl- or triaryl-substituted organometallic compounds formed by the method of the invention, in general, are more toxic to fungus and algae and the like than the disubstituted organometallics, while the monosubstituted organometallics are even less toxic. However, it is to be understood that any of mono, di or tri-organo substituted metallics are applicable to the novel synthesis method of the invention without any particular limitations.

In a further preferred embodiment of the invention, the three substituents $R_1$, $R_2$, and $R_3$ of the triorganometallic compound of Formula IV described herein, other than the nucleophilic group X', are selected to include two methyl groups and the third substituent being an oleate group. This particular combination of organo substituents has been found to provide an advantageous toxic effect on fungus, algae and the like.

In this application:

"organometallic" means compounds possessing a metal atom, which is not inclusive of either Si or C or other nonmetals, directly bonded to one or more carbon atoms;

a "triorganometallic" compound of the invention means three organic substituents are directly bonded to the metal atom in the organometallic compound;

a "trialkylorganometallic" compound of the invention means three alkyl substituents are directly bonded to the metal atom as the organometallic compound;

a "triarylorganometallic" compound of the invention means three aryl substituents are directly bonded to the metal atom as the organometallic compound;

"triorganometallic acrylamide(s)" means those structures of Formula III herein in which n=0 and 1, respectively. Although IUPAC nomenclature would dictate complex names for these materials, in the interest of simplicity, the commonly used name "acrylamide(s)" is employed herein;

"nucleophile" means an ion or molecule that donates a pair of electrons to an atomic nucleus to form a covalent bond;

"alkyl" and "alkylene" mean the monovalent and divalent residues remaining after removal of one and two hydrogen atoms, respectively, from a linear or branched chain hydrocarbon having 1 to 20 carbon atoms;

"lower alkyl" means $C_1$ to $C_4$ alkyl;

"aryl" and "arylene" mean the monovalent and divalent residues remaining after removal of one or two hydrogen atoms, respectively, from an aromatic compound (single ring and multi- and fused-ring) having 5 to 12 ring atoms and includes substituted aromatics such as lower alkaryl and aralkyl, lower alkoxy, N,N-di(lower alkyl)amino, nitro, cyano, halo, and lower alkyl carboxylic ester, wherein "lower" means $C_1$ to $C_4$;

"azlactone" means 2-oxazolin-5-one groups of Formula I and 2-oxazin-6-one of Formula II:

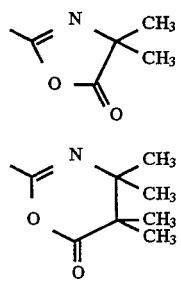

"cycloalkyl" means the monovalent residue remaining after removal of a hydrogen atom from a cyclic hydrocarbon having 3 to 12 carbon atoms;

"microbes" means materials encompassing, but not restricted to, all bacterial, fungal, and algal organisms;

"soluble" means at least 0.1 gram dissolves in 100 gram of any solvent at 23° C.; and "insoluble" means less than 0.1 gram dissolves in 100 gram of solvent at 23° C.;

"low molecular weight" refers to soluble compounds of less than 1000 mass units (number average), whereas "high molecular weight" refers to soluble polymers at least 1000 mass units (number average) up to essentially infinite molecular weight and insoluble polymers and materials whose molecular weight are essentially infinite.

The reaction products of this invention have wide application as antifouling agents, especially as an additive in organic binders used in ceramic applications. For instance, the novel organometallic acrylamides of the invention are easily dispersed in organic binder systems as carriers which are, in turn, applied to inorganic granules such as colored roofing and construction granules, flooring material and COLORQUARTZ™. Other substrates which can have antifouling properties imbued to their surfaces by the compounds of this invention include, but are not limited to, plastics, reinforced plastics such as glass-fiber reinforced plastics, metals, glasses, ceramics, rubber, nonwovens, woven fabrics, and woods.

Other advantageous features, constructs, aspects and utilities of the invention will become apparent from the following detailed description and working examples.

DETAILED DESCRIPTION OF THE PREFERRED EMBODIMENTS

The present invention provides a novel method whereby an azlactone is reacted with an organometallic nucleophile compound to form organometallic acrylamides. The reaction can proceed without the need for noxious solvents and the reaction products are free of undesirable by-products.

In one particular embodiment, the present invention provides a novel method for forming a class of triorganometallic acrylamides that can be represented as having the following general Formula III:

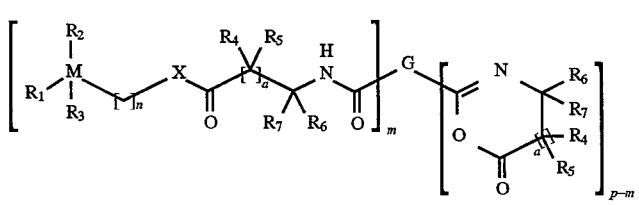

wherein:
- $R_1$, $R_2$, and $R_3$ can be the same or different and can be alkyl or aryl groups, preferably with the proviso that no more than two of groups $R_1$, $R_2$, and $R^3$ can be methyl at the same time;
- M can be a metal from either Groups 3–12 in the Periodic Chart of the Elements with the proviso that M cannot represent nonmetals such as Si or C;
- n is 0–4;
- X can be an oxygen atom, a sulfur atom,

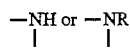

where R is 1–4C alkyl;
- $R_4$ and $R^5$ are independently hydrogen or lower alkyl;
- a is 0 or 1;
- $R_6$ and $R_7$ independently can be alkyl, preferably methyl, cycloalkyl, or aryl group, or $R_6$ and $R_7$ taken together with the carbon to which they are joined can form a carbocyclic ring containing 4 to 12 ring atoms, with the proviso that only one of $R_6$ and $R_7$ can be aryl;
- G is any polyvalent linking group unreactive with azlactone when m is at least 2; or G is any monovalent terminal group unreactive with azlactone when p=m=1;
- m can have any positive integral value from 1 to p;
- p can have any positive integral value from 1 to infinity when the number of azlactone groups is essentially that value (i.e., infinite) as part of an insoluble crosslinked network;
- G can contain the functionality that may be desired to be imparted to the organometallic bearing substrate provided the functionality is unreactive with azlactone. G can be an alkyl or aryl group or G can be quite complex containing multiple functional groups with no particular limitation as long as they meet the requirement of nonreactivity with azlactone. The molecular weight Of G can vary from 15, when G is methyl and, p−m=0, to several million (such as 5 million or more) when G is a soluble polymer group, and finally, to infinity, when G is an insoluble, crosslinked polymeric network. G can have bonding capacity of 1, as when it is a terminal group, to essentially infinite bonding capacity as when it is linking group in a glassy network. Functional groups that can be incorporated in G include one or more of alkyl, aryl, amide, ester, nitrile, nitro, sulfoxide, sulfone, azide, isocyanate, isothiocyanate, tertiary amine, ether, urethane, quaternary ammonium and phosphonium, halogen, and the like, wherein the functional groups requiring substituents are substituted with hydrogen where appropriate or lower alkyl so as not to mask the effect of the functional groups.

The novel triorganometallic acrylamides of the invention (Formula III) are the nucleophilic addition reaction products of triorganometallic- alcohols, amines or thiols having the general Formula IV:

wherein $R^1$, $R^2$, $R^3$, M, and n are as previously defined, while X' is —OH, —SH, —$NH_2$, or —NHR where R is alkyl such as 1–4C alkyl; and an azlactone of Formula V:

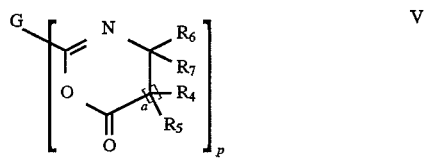

wherein: $R^4$, $R^5$, $R^6$, $R^7$, p, a, and G are as defined above.

The novel chemical reaction scheme contemplated by this invention for making the Formula III compounds from the Formula IV and Formula V compounds is shown below:

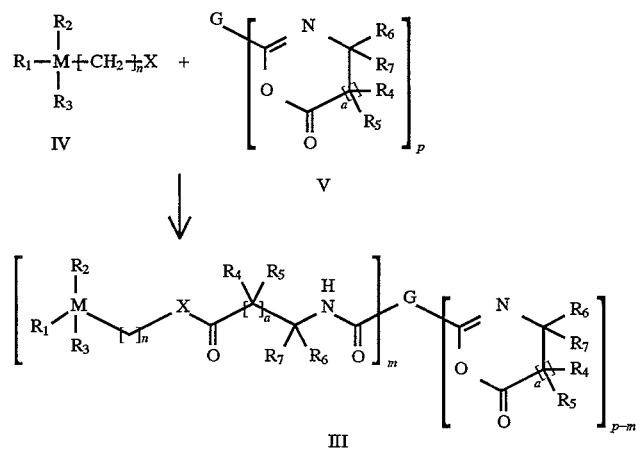

Suitable organometallic reactants of Formula IV of the invention include any soluble, low or high molecular weight material that contains at least one group among

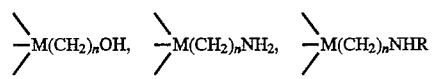

where R is alkyl such as 1–4C alkyl, and

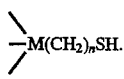

The use of n=1–4 is preferred as the provision of intervening methylene group(s) provides a desirable steric configuration by spacing the nucleophilic group from the remainder of the molecule.

For purposes of this invention, M does not represent atoms such as Si or C, nor does M represent other traditionally recognized nonmetallics such as halogen atoms. The use of Sn atom as M is preferred based on the fact that this atom affords highly effective antifouling and antimicrobial action. It is thought that M also can represent other metal atoms such as Ge, Pb, Cd, Hg, As, Ti, to name a few; although these atoms, other than Ge, are not preferred from a practical standpoint as they can raise more difficult environmental and health regulatory issues.

It is preferred that $R^1$, $R^2$, or $R^3$ represent a lower alkyl group of 1–4C, especially preferred are 1–4C n-alkyl chains. An increase beyond n-butyl in length for an n-alkyl chain tends to produce a dramatic drop in the biological activity where the organometallic nucleophile derivative can become nontoxic to all living organisms including the targeted microbes. Also, in one preferred embodiment of the invention, one of $R^1$, $R^2$, or $R^3$ represents an oleate group, i.e. an $CH_3(C_2)_7CH=CH(C_2)_7C(O)O$— group, in view of its excellent fungicidal properties.

Representative organometallic reactants include:

(1) Low molecular weight, soluble organometallic materials are compounds that are stable and insoluble. Compounds of this type include triphenylhydroxytin, dimethylhydroxy(oleate)tin, and, 3-aminopropyltributylgermane. The preferred organometallic nucleophile is dimethylhydroxy(oleate)tin because of its reactivity and biotoxicity towards microbes. These compounds are commercially available from Gelest Inc., Tullytown, Pa.

(2) High molecular weight, soluble organometallic materials are compounds which are referred to as polymeric in nature. Compounds of this type include n-butyltinhydroxide oxide. This compound is commercially available from Gelest Inc., Tullytown, Pa.

Suitable azlactone reactants of the invention include any soluble or insoluble, low or high molecular weight material that contains at least one azlactone group. 2-alkenyl azlactones are well-known and their synthesis, physical and chemical properties, homo- and copolymerization behavior, and applications are discussed in the above-mentioned article by J. K. Rasmussen, S. M. Heilmann, and L. R. Krepski, entitled "POLYAZLACTONES", Encycl. Poly. Sci. Eng., 11, 558–571, 1988.

When the value of p in Formula V is one, the azlactone group, when reacted, serves primarily to covalently link the organometallic substrate with the G group, and the property or modification desired to be imparted to the organometallic reactant must be present in G. G may contain one or more functional groups which themselves do not react with the azlactone including alkyl, aryl, amide, ester, nitrile, nitro, sulfoxide, sulfone, azide, isocyanate, isothiocyanate, tertiary amine, ether, urethane, quaternary ammonium and phosphonium, halogen, and the like, wherein the functional groups requiring substituents are substituted with hydrogen where appropriate or lower alkyl so as not to mask the effect of the functional groups. When the value of p in Formula V is not a value of one, the G group may provide both the modifying functional groups or the linkage to other azlactone groups or both. This duality of purpose is especially true with high molecular weight, 2-alkenyl azlactone containing copolymeric G groups. Useful amounts to initiate the nucleophilic addition reaction between the triorganometallic species and azlactone can be in the range of 0.1 to 99.9 equivalents to 99.9 to 0.1 equivalents, preferably 1:99 to 99:1 equivalents, more preferably 10:90 to 90:10. Representative azlactone materials for use in the reaction of the invention include:

(1) Low molecular weight soluble azlactone materials include monoazlactones such as 2-alkyl and 2-aryl substituted azlactones, optionally containing the aforementioned functional groups, and polyazlactones of the type disclosed in U.S. Pat. No 4,485,236, which is incorporated by reference, as well as those reported in the general literature by S. M. Heilmann, et al., J. Polymer Sci.: Polymer Chem. Ed., 24, 1 (1986), also incorporated herein by reference. Preferred low molecular weight soluble azlactones include 2-vinyl-4,4-dimethyl-2-oxazolin-5-one, 2-isopropenyl-4,4-dimethyl-2-oxazolin-5-one, 2-vinyl-4-ethyl-4-methyl-2-oxazolin-5-one, 2-vinyl-4,4-diethyl-2-oxazolin-5-one, 2-vinyl-4-methyl-4-phenyl-2-oxazolin-5-one, 2-isopropenyl-4,4-tetramethylene-2-oxazolin-5-one, 2-vinyl-4,4-pentamethylene-2-oxazolin-5-one, 2-vinyl-4,4-dimethyl-2-oxazolin-6-one, 2-dodecyl-4,4-dimethylazlactone, 1,4-bis[(4,4-dimethyl-2-oxazolin-5-one-2-yl)] butane, 1,5-bis[(2-(4,4-dimethyl-2-oxazolin-5-one-2-yl) ethylthio]-3-oxapentane, and the like. The preferred 2-alkenyl azlactone because of its reactivity and commercial availability is 2-vinyl-4,4-dimethyl-2-oxazolin-5-one (SNPE Inc., Princeton, N.J.).

(2) High molecular weight, soluble azlactone materials include any free radical addition copolymers of 2-alkenyl azlactones, such as those disclosed in U.S. Pat. No. 4,304,705, incorporated herein by reference. Preferred high molecular weight soluble azlactones include copolymers containing at least one part by weight of an 2-alkenyl azlactone such as 2-vinyl-4,4-dimethylazlactone and vinyl chloride, ethyl acrylate, styrene, methyl methacrylate, acryloxytri-n-butyltin, acryloxytriphenyltin, allyltrimethylgermane, allyltriethylgermane, copper II methacryloxyethyl acetoacetate, methacryloxymethyltrimethylgermane, methacryloxydiphenylantimony, and combinations thereof.

(3) Insoluble azlactone materials possessing essentially an infinite molecular weight include those 2-alkenyl azlactone copolymers with the aforementioned mono(ethylenically unsaturated) comonomers and at least one multi (ethylenically unsaturated) comonomer, whose copolymerization results in the joining of polymer chains causing crosslinking and insolubilization. Suitable multi (ethylenically unsaturated) comonomers include but are not limited to those disclosed in U.S. Pat. No. 4,379,201, also incorporated herein by reference. Since these copolymers, once formed, are insoluble and thermosetting, they are generally prepared directly in the end-use configuration. Insoluble azlactone materials useful in the present invention include the crosslinked, hydrophilic, azlactone functional polymer beads disclosed in U.S. Pat. No. 4,737,560, which is also incorporated herein by reference.

The formation of the reaction products of the invention between azlactone and the organometallic nucleophile is facilitated by the presence of a catalyst. Useful catalysts include 1,8-diazabicyclo[5.4.0]undec-7-ene (DBU), 1,5-diazabicyclo[4.3.0]non-5-ene (DBN), 1,4-diazabicyclo [2.2.2]octane (DABCO), triethylamine, tripropylamine, tributylamine, trihexylamine, trioctylamine, and trihexylamine. These compounds are commercially available from Aldrich Chemical Co., Milwaukee, Wis. Polymeric-supported catalysts such as those described by Tomoi in *Makromol. Chem.* 185, 2117, 1984 can also be employed as a useful catalyst. The use of ion-exchange resins can also be employed as useful catalysts. Useful catalysts include Amberlite IRA-68 (available from Rohm & Hass, Philadelphia, Pa.), Amberlite IRA-938, Amberlite IRA-400, Amberlite MA-401 S, and Amberlite IRA-410 (available from Malinckrodt Specialty Chemicals Co., Paris, Ky.). Molar concentrations of the catalysts range from 0.1 to 20 weight percent, preferably 0.25 to 5.0 weight percent, and most preferably 0.5 to 2.0 weight percent based on the azlactone reactant; triethylamine and Amberlite IRA-68 are preferred.

In a typical procedure of the reaction of the invention, equal molar quantities of azlactone and organometallic nucleophile are mixed with the catalyst in absence of solvent, i.e., the reaction can be performed "neat". When using the preferred catalysts and a solvent-free reaction solution, it is more likely that a mildly exothermic reaction will ensue, and the reaction is generally completed, as determined by infrared spectroscopy, when the reaction temperature is observed to return to ambient temperature.

Alternatively, solvents may be employed with the provision that they not react with the azlactone or catalyst under the reaction conditions. Suitable organic solvents include ethyl acetate, toluene, and tetrahydrofuran (available from Aldrich Chemical Co., Milwaukee, Wis.). Although not typically required, in some instances, the solvents might desirable for practical reasons as a heat sink and/or dispersion medium for the reactants.

In the case of ion-exchange resins, the catalyst may be removed from the reaction product by filtration without leaving any unwanted ion in the organometallic acrylamide. The catalyst may be rejuvenated by washing the ion exchange resin with alkali. With other catalysts and when solvents are employed, warming the reaction mixture will hasten completion of reaction. It is generally advisable to add a free radical stabilizer such as phenothiazine or 2,6-di-t-butyl-p-cresol in concentrations by weight based on reaction product of from 0.001 to 1.0 percent, preferably 0.05 to 0.15 percent. Suitable warming temperatures are from 40°–80° C.; preferably 40°–65° C., for a period of 0.5 to 12 hours, preferably 0.5 to 2 hours.

When employing low molecular weight soluble azlactones such as 2-alkenyl azlactones, soluble organometallic acrylamide monomers are prepared. By reason of the unsaturation of the organometallic acrylamide monomers, novel and useful coating compositions are obtained by mixing with other curable monomers. Specific examples of such curable monomers include: styrene and monofunctional acrylate esters (up to 20C's) such as butyl acrylate, ethyl acrylate, methyl acrylate, methyl methacrylate, 2-ethylhexyl acrylate, cyclohexylmethyl acrylate, and phenethylacrylate. Organometallic monomers may also be employed as such curable monomers such as acryloxytri-n-butyltin, acryloxytriphenyltin, allyltrimethylgermane, allyltriethylgermane, copper II methacryloxyethyl acetoacetate, methacryloxymethyltrimethylgermane, methacryloxydiphenylantimony. Combinations of non-organometallic and organometallic monomers also are contemplated as being useful as such curable monomers.

The organometallic acrylamide products of this invention further can be copolymerized with any compatible actinic cured monomers such as (meth)acrylate, allyl, styryl, and the like head groups. The polymeric reaction products of this invention can be used as antifouling agents as well as for organic binders for ceramic applications.

Actinic radiation necessary for the polymerization of the monomeric composition to form the polymeric coating compositions of the invention can be supplied in two forms: high energy electrons (emitted from commercial electron beam generators) and ultraviolet light. With ultraviolet light another component is generally necessary for the light to be absorbed and for polymerization to be initiated. These latter functions are most commonly accomplished by addition of a so-called photoinitiator to the system in a concentration range of from 0.1 to 5.0 percent, preferably 1.0 to 3.0 percent, by weight (based on polymerizable monomers). Useful photoinitators include acyloins and acyloin ethers which are commercially available.

Several reaction products of this invention, particularly those incorporating a Sn-based organometallic nucleophile, can have wide application as antifouling agents. One desirable application of the reaction products of the invention is as an additive in organic binders used in ceramic applications. For instance, the novel organometallic acrylamides of the invention are easily dispersed in organic binder systems as carriers which are, in turn, applied to inorganic granules such as colored roofing and construction granules, flooring material and COLORQUARTZ™, a product of Minnesota Mining and Manufacturing Co., St. Paul Minnesota. Other substrates which can have antifouling properties imparted to their surfaces by the compounds of this invention include, but are not limited to, plastics, reinforced plastics such as glass-fiber reinforced plastics, metals, glasses, rubber, ceramics, nonwovens, woven fabrics, and woods.

The reaction products of the invention can be added to these exemplary substrates in any convenient manner. For example, the reaction products can be dispersed in the substrate material, such as in the case of plastics or ceramics, or by topcoat application, such as in the case of metals, glasses, rubber, nonwovens, wovens or woods. The effective amount of antifouling agent needed to prevent the proliferation of or eliminate existing targeted organisms may vary depending on the particular application involved. In any event, it will be understood that an effective amount can be determined empirically by one of skill for the particular substrate and manner chosen of applying the antifouling agent thereto. For example, in the case of algae, the antifouling effect can be visually monitored.

The antifouling agents of the invention, such as those formed from a Sn-based organometallic nucleophile, are generally effective in most instances in concentrations of at least 0.1 mg/liter dispersant, and preferred concentrations are those exceeding 1 mg/liter dispersant, such as 1 to 1,000 mg/liter. However, it is to be understood that the antifouling agent of the invention may be effective in even lower concentrations as low as 0.01 mg/liter in certain environments where the potency of the particular antifouling agent compound of the invention is relatively strong and/or the microbial growth potential is somewhat diminished.

Objects and advantages of this invention are further illustrated by the following examples, but the particular materials and amounts thereof recited in these examples, as well as other conditions and details, should not be construed to unduly limit the invention.

EXAMPLES

Example 1

The reaction of 2-vinyl-4,4-dimethylazlactone with triphenyltin hydroxide is described.

Triphenyltin hydroxide (available from Gelest Inc., Tullytown, Pa.) (39.27 grams, 0.107 mole) and 2-vinyl-4,4-dimethylazlactone (VDM) (available from SNPE, Inc., Princeton, N.J.) (14.9 grams, 0.107 mole) were mixed to facilitate a heterogenous mixture. To this mixture was added methyl ethyl ketone (33 grams) and 1,8-diazabicyclo[5.4.0]undec-7-ene (available from Aldrich Chemical Corp., Milwaukee, Wis.) (0.30 gram, $2.0 \times 10^{-3}$ mole). The reaction mixture was shaken for approximately 10 minutes and then allowed to stand at room temperature for thirty hours. An infrared spectrum showed characteristic absorptions for the acrylamide product: 3.05 (NH stretch), 5.75 (ester C=O), 6.05 (amide C=O), 6.15 (C=C), and 6.50 (amide) at 11 microns. The crude product was isolated by decantation to yield the organometallic triphenyltin acrylamide as a solid.

Example 2

The reaction of 2-vinyl-4,4-dimethylazlactone with dimethylhydroxy(oleate)tin is described.

In a similar fashion to Example 1, dimethylhydroxy (oleate)tin (44.24 gram, 0.107 mole) was reacted with 2-vinyl-4,4-dimethylazlactone (14.9 gram, 0.107 mole) in the absence of solvent. The catalyst, 1,8-diazabicyclo[5.4.0]undec-7-ene (0.30 gram, $2.0 \times 10^{-3}$ mole) was utilized and the homogenous solutions was shaken for 10 minutes at room temperature. A slight exotherm was apparent and the reaction mixture was heated to 60° C. for 30 hours. A solid material had formed and was collected and purified by recrystallization from ethyl acetate: pentane. Infrared spectroscopy and nuclear magnetic resonance spectroscopy confirmed the structure of the dimethyl(oleate) tin acrylamide monomer.

Example 3

A similar procedure was used as in Example 1 except that 3-aminopropyltributyl germane (0.50 gram, 0.002 mole) was reacted with 2-vinyl-4,4-dimethylazlactone (0.24 gram, 0.002 mole) in the absence of solvent. An exothermic reaction was readily apparent upon combination of the reactants and the solution crystallized within a few minutes. The microcrystalline solid which formed was washed with methylethyl ketone and was dried overnight in a vacuum dessicator. Infrared spectroscopy and nuclear magnetic resonance spectroscopy confirmed the structure of the reaction product to be aminopropyltributylgermane acrylamide monomer.

Example 4

The preparation of a polymeric organotin acrylamide composition of the invention is described.

A 100 mL glass bottle was charged with poly-2-vinyl-4,4-dimethylazlactone-co-methylmethacrylate (prepared as described in U.S. Pat. No. 4,304,705) (15.0 grams, 30% solids in methyl ethyl ketone, $5.39 \times 10^{-3}$ mole), dimethylhydroxy(oleate)tin (2.45 gram, $5.93 \times 10^{-3}$ mole), and three drops of 1,8-diazabicyclo[5.4.0]undec-7-ene. The reaction mixture was shaken for 10 minutes at room temperature and the solution became extremely viscous. The reaction mixture was then heated to 50° C. for 46 hours. Inspection of the carbonyl band by infrared spectroscopy revealed that 100% reaction had transpired.

Example 5

In a similar manner to Example 4, poly-2-vinyl-4,4-dimethylazlactone-co-methylmethacrylate (prepared as described in U.S. Pat. No. 4,304,705) (15.0 grams, 30% solids in methyl ethyl ketone, $5.39 \times 10^{-3}$ moles) was reacted with triphenyltin hydroxide (2.18 gram, $5.93 \times 10^{-3}$ mole). After 46 hours at 50° C., infrared spectroscopy analysis indicated a 100% conversion to the triphenyltin acrylamide adduct.

Example 6

The evaluation of the biocidal activity of triorganometallic acrylamide polymers is described.

The trialkyl ortiphenyl tin acrylamide copolymers from Examples 4 and 5,respectively each were evaluated as antifouling agents against blue-green and green algae as Samples 1 and 2, respectively, which were formulated as summarized in Table 1. The polyacrylamide trialkyl ortiphenyl tin coatings were formed by brush applying each of the compositions of Table 1 onto a separate asphalt shingle panel, each of which is infested with blue-green and green algae over the entirety of the surface of each panel. A shingle area of 29.5×13.5 cm (398.25 cm$^2$) was coated in each run by a sufficient amount of biocidal composition to wet the surfaces. The algae infestation on each test shingle was clearly discernible to the naked eye before treatment.

Also, untreated infested shingles, designated Sample U, were positioned in the same rack above and below the shingles treated by Samples 1 and 2 as a control.

A comparison experiment also was run on a similarly infested shingle for comparative purposes using a polymeric biocidal material, designated as Sample C, based on a tributyltin ester of methacrylic acid in 16 wt. % solids in a CHCl$_3$ solvent.

The infested asphalt shingles, which were coated with compositions described in this example, all were placed on north-facing racks in Houston, Tex.

As another experiment, the trialkyl tin acrylamide copolymer from Example 4 again was provided as 10 wt.% solids in a CHCl$_3$ solvent, as Sample 2A, and was applied by brush to a shingle panel infested with green algae. This panel was similarly exposed on a north-facing rack and was shaded to prevent desiccation of the algae.

All amounts in Table 1 are described in terms of the weight% of antifouling agent ("AA") solids based on total weight of CHCl$_3$ solvent and solids.

TABLE 1

| Sample | wt. % AA | % Removal | Leaching |
| --- | --- | --- | --- |
| 1 | 10 | >95 | none |
| 2 | 16 | >95 | none |
| 2A | 10 | 100 | none |
| U | 0 | 0 | — |
| C | 16 | >95 | yes |

As summarized in Table 1, the infested asphalt shingles, which had been treated by Samples 1 and 2 representing the invention, all showed greater than 95% reduced amounts of algae infestation, based on surface area where algae was completely removed/total area, within 10 days, as evidenced by the visually discernible removal of the discoloration associated with the algae on the shingles to reveal the original coloration of the shingles. Likewise, inhibition of algae also was noted for Sample 2A by removal of all the green algae discoloration on the shingle within 10 days.

In contrast, the untreated control shingles of Sample U showed no clean-up or removal of the algae.

The triorganometallic acrylamide copolymers of Samples 1, 2 and 2A also were observed to show effectiveness against algae on a slightly shorter time frame than Sample C. While the amount of algae removal ultimately effected by comparison Sample C was approximately the same as that achieved with Samples 1 and 2 representing the invention, a leaching problem was observed to occur for the comparison Sample C. That is, the inventive biocidal materials of Samples 1, 2 and 2A did not migrate away from the shingle surface areas to which they were first applied.

In contrast, the comparative biocidal material used in Sample C leached away from the applied surface onto neighboring surfaces which had not been originally treated. That is to say, Sample C visually showed a great deal of migration into noncoated areas on the shingle after application as indicated by inhibition of algae growth on shingle panels located lower and beneath the bottom edge of the treated shingles on the same support surface. This is a highly undesirable attribute as it indicates that the antifouling or toxic action is not generally limited to the treated site, but instead the treating agent, as it migrated, also infiltrated the surrounding vicinity.

Various modifications and alterations of this invention will become apparent to those skilled in the art without departing from the scope and spirit of this invention, and it should be understood that this invention is not to be unduly limited to the illustrative embodiments set forth herein.

We claim:

1. A method of making an organometallic acrylamide comprising contacting an azlactone with an organometallic nucleophile compound which is effective to ring-open said azlactone and form said organometallic acrylamide therewith, wherein said organometallic nucleophile compound has the formula:

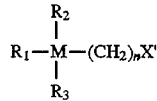

where X' is —OH, —SH, —NH$_2$, or —NHR, where R is an alkyl group; n is an integer of from 0 to 4; R$_1$, R$_2$, and R$_3$ each is independently an alkyl group or an aryl group or an oleate, with the proviso that not more than two of R$_1$, R$_2$, and R$_3$ can represent CH$_3$ at the same time; and M represents Sn, Ge, or Pb.

2. The method of claim 1, wherein said azlactone has the formula:

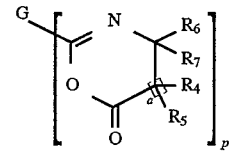

where R$_4$ and R$_5$ each independently represents hydrogen or a 1–4C alkyl group; a is 0 or 1; R$_6$ and R$_7$ each independently represents an acyclic alkyl group, a cycloalkyl group, an aryl group or an aralkyl group, or R$_6$ and R$_7$, taken together with the carbon to which R$_6$ and R$_7$ are joined can form a carbocyclic ring containing 4 to 12 ring atoms, with the proviso that only one of R$_6$ and R$_7$ can be aryl; G represents a polyvalent linking group unreactive with azlactone when m is at least 2, or G represents a monovalent terminal group unreactive with azlactone when p=m=1; p is an integer value of from 1 or greater; and m is an integer value of 1 to p.

3. The method of claim 1, wherein said azlactone and said organometallic nucleophile compound are mixed in a substantially equimolar ratio in the presence of a catalyst.

4. The method of claim 1, wherein said contacting is conducted in the presence of a catalyst selected from the group consisting of 1,8-diazabicyclo[5.4.0.]undec-7-ene, 1,5-diazabicyclo-[4.3.0]non-5-ene, 1,4-diazabicyclo[2.2.2]octane, triethylamine, tripropylamine, tributylamine, trihexylamine, trioctylamine, and trihexylamine.

5. The method of claim 4, wherein said catalyst is used in an amount of from 0.1 to 20 percent by weight based on weight of said azlactone.

6. The method of claim 1, wherein one of R$_1$, R$_2$, and R$_3$ represents an CH$_3$(CH$_2$)$_7$CH=CH(CH$_2$)$_7$C(O)O— group.

* * * * *

UNITED STATES PATENT AND TRADEMARK OFFICE
CERTIFICATE OF CORRECTION

PATENT NO.: 5,639,843
DATED: June 17, 1997
INVENTOR(S): Stefan A. Babirad and Stuart Bigham It is certified that error appears in the above-identified patent and that said Letters Patent is hereby corrected as shown below:

Column 1, line 28, delete "163".

Column 7, line 59, delete "Of" and insert therefore --of--.

Column 8, line 18, delete "$R^1, R^2, R^3$" and insert therefore --$R_1, R_2, R_3$--.

Column 8, line 30, delete "$R^4, R^5, R^6, R^7$" and insert therefore --$R_4, R_5, R_6, R_7$--.

Column 9, line 29, delete "$CH_3(C_2)_7CH=CH(C_2)_7C(O)O$" and insert therefor --$CH_3(CH_2)_7CH=CH(CH_2)_7C(O)O$--.

Column 14, line 14, delete "ortiphenyl" and insert therefore --or tiphenyl--.

Column 14, line 18, delete "ortiphenyl" and insert therefore --or tiphenyl--.

Signed and Sealed this

Twenty-eighth Day of November, 2000

Attest:

Q. TODD DICKINSON

Attesting Officer

Director of Patents and Trademarks